(12) United States Patent
Marcotte et al.

(10) Patent No.: US 9,050,446 B2
(45) Date of Patent: Jun. 9, 2015

(54) PORT WITH CONDUIT WRAPAROUND FEATURE

(75) Inventors: Amy L. Marcotte, Mason, OH (US); Scott A. Woodruff, Cincinnati, OH (US); Karalyn R. Tellio, Cincinnati, OH (US); Michael J. Vendely, Lebanon, OH (US); Andrew T. Beckman, Cincinnati, OH (US); Stephen M. Torain, Cincinnati, OH (US); Craig D. Stover, Williamston, MI (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 308 days.

(21) Appl. No.: 12/946,936

(22) Filed: Nov. 16, 2010

(65) Prior Publication Data

US 2012/0123198 A1 May 17, 2012

(51) Int. Cl.
| | |
|---|---|
| *A61M 37/00* | (2006.01) |
| *A61M 39/02* | (2006.01) |
| *A61M 39/10* | (2006.01) |
| *A61M 39/12* | (2006.01) |
| *A61F 5/00* | (2006.01) |

(52) U.S. Cl.
CPC .......... *A61M 39/0208* (2013.01); *A61F 5/0056* (2013.01); *A61M 39/1011* (2013.01); *A61M 39/12* (2013.01); *A61M 2039/0223* (2013.01); *A61M 2039/0226* (2013.01)

(58) Field of Classification Search
CPC ..................... A61M 39/0208; A61M 39/0247; A61M 39/04; A61M 2039/0208; A61M 2039/0235; A61M 2039/0255; A61M 5/14276; A61F 5/005; A61F 5/0053; A61F 5/0056; A61F 5/0059; A61F 5/0063

USPC ............................ 600/37; 606/151; 604/175, 604/288.01-288.04
See application file for complete search history.

(56) References Cited

U.S. PATENT DOCUMENTS

| | | | | |
|---|---|---|---|---|
| 4,311,148 A | * | 1/1982 | Courtney et al. | .............. 604/175 |
| 4,568,345 A | * | 2/1986 | Keilman et al. | ............... 604/403 |

(Continued)

FOREIGN PATENT DOCUMENTS

| | | |
|---|---|---|
| EP | 1 671 590 | 6/2006 |
| WO | WO 2009/129474 | 10/2009 |
| WO | WO 2011/137036 | 11/2011 |

OTHER PUBLICATIONS

U.S. Appl. No. 12/946,923, Nov. 16, 2010, Woodruff et al.

(Continued)

*Primary Examiner* — Jacqueline Cheng
*Assistant Examiner* — Eileen Hyde

(57) ABSTRACT

An injection port includes a port body having a fluid reservoir and a connector in fluid communication with the reservoir. The injection port further includes a conduit protection feature that is configured to protect against kinking of the conduit, decoupling of the conduit from the connector, or penetration of the conduit by a needle. The protection feature may include an anchor for anchoring the conduit to tissue to reduce conduit movement. The protection feature may include a recess that is configured to receive part of the conduit. The protection feature may include a bend formed in the connector to reduce transverse stresses in the conduit. The protection feature may include a bell-shaped shroud encompassing the connector. A sleeve may further protect the conduit and/or the coupling between the connector and the conduit.

11 Claims, 6 Drawing Sheets

(56) References Cited

U.S. PATENT DOCUMENTS

| | | | |
|---|---|---|---|
| 5,356,381 A * | 10/1994 | Ensminger et al. | 604/288.03 |
| 5,417,656 A * | 5/1995 | Ensminger et al. | 604/288.03 |
| 5,613,945 A * | 3/1997 | Cai et al. | 604/288.02 |
| 5,792,104 A | 8/1998 | Speckman et al. | |
| 5,972,017 A * | 10/1999 | Berg et al. | 606/198 |
| 6,067,991 A | 5/2000 | Forsell | |
| 6,290,677 B1 | 9/2001 | Arai et al. | |
| 6,379,816 B1 | 4/2002 | DeLoose et al. | |
| 6,461,292 B1 | 10/2002 | Forsell | |
| 6,470,892 B1 | 10/2002 | Forsell | |
| 7,351,240 B2 | 4/2008 | Hassler, Jr. et al. | |
| 7,390,294 B2 | 6/2008 | Hassler, Jr. | |
| 7,416,528 B2 | 8/2008 | Crawford et al. | |
| 7,442,165 B2 | 10/2008 | Forsell | |
| 7,621,863 B2 | 11/2009 | Forsell | |
| 7,632,263 B2 | 12/2009 | Denoth et al. | |
| 7,699,770 B2 | 4/2010 | Hassler, Jr. et al. | |
| 7,775,215 B2 | 8/2010 | Hassler, Jr. et al. | |
| 7,850,660 B2 | 12/2010 | Uth et al. | |
| 2005/0192559 A1 | 9/2005 | Michels et al. | |
| 2005/0242579 A1 * | 11/2005 | Bright et al. | 285/256 |
| 2005/0283118 A1 * | 12/2005 | Uth et al. | 604/175 |
| 2006/0199997 A1 | 9/2006 | Hassler, Jr. et al. | |
| 2009/0062826 A1 * | 3/2009 | Steffen | 606/157 |
| 2010/0211085 A1 * | 8/2010 | Uth et al. | 606/151 |
| 2010/0312193 A1 * | 12/2010 | Stratton et al. | 604/175 |
| 2011/0213308 A1 * | 9/2011 | Popowski et al. | 604/175 |
| 2011/0270019 A1 * | 11/2011 | Deuel et al. | 600/37 |
| 2012/0109068 A1 * | 5/2012 | Vendely | 604/175 |

OTHER PUBLICATIONS

International Search Report dated May 7, 2012 for Application No. PCT/US2011/060896.

* cited by examiner

PORT WITH CONDUIT WRAPAROUND FEATURE

BACKGROUND

A variety of systems and devices have been made and used for treating morbid obesity. Some such systems and devices include adjustable gastric band systems, which are operable to restrict the flow of food from the esophagus into the stomach. Some gastric bands include a fluid-filled elastomeric bladder with fixed endpoints that encircles the stomach just inferior to the gastro-esophageal junction. When fluid is added to the bladder, the band expands against the stomach, creating a food intake restriction or stoma in the stomach. To decrease this restriction, fluid is removed from the bladder. Examples of gastric bands are disclosed in U.S. Pat. No. 7,416,528, entitled "Latching Device for Gastric Band," issued Aug. 26, 2008, the disclosure of which is incorporated by reference herein. Another example of such an adjustable gastric band is disclosed in U.S. Pat. No. 6,067,991, entitled "Mechanical Food Intake Restriction Device," issued May 30, 2000, the disclosure of which is incorporated by reference herein.

To the extent that an adjustable gastric band system includes an injection port configured to receive the needle of a syringe assembly to add or withdraw fluid to or from the gastric band, those of ordinary skill in the art will appreciate that it may be desirable in some settings to locate both the injection port and, more specifically, the center of the injection port (e.g., when the septum of the injection port is at the center of the injection port). Locating the approximate center of the injection port with some degree of accuracy may facilitate addition or withdrawal of fluid via the injection port to adjust the gastric band system. One example of a system and method for identifying the location of an injection port is disclosed in U.S. Pub. No. 2006/0211914, entitled "System and Method for Determining Implanted Device Positioning and Obtaining Pressure Data" published Sep. 21, 2006, and issued Aug. 17, 2010 as U.S. Pat. No. 7,775,215, the disclosure of which is incorporated by reference herein.

Those of ordinary skill in the art will appreciate that it may be advantageous in certain circumstances to sense pressure, strain, and/or other parameters associated with operation of a gastric band device. In some settings, it may be desirable to obtain data indicative of the pressure of fluid in a gastric band. Various examples of methods and devices for obtaining pressure data and other types of data are disclosed in U.S. Pub. No. 2006/0189888, entitled "Device for Non-Invasive Measurement of Fluid Pressure in an Adjustable Restriction Device," published Aug. 24, 2006, and issued Apr. 20, 2010 as U.S. Pat. No. 7,699,770, the disclosure of which is incorporated by reference herein. Additional examples of methods and devices for obtaining pressure data and other types of data are disclosed in U.S. Pub. No. 2006/0199997, entitled "Monitoring of a Food Intake Restriction Device," published Sep. 7, 2006, and issued Sep. 13, 2011 as U.S. Pat. No. 8,016,745, the disclosure of which is incorporated by reference herein. Such parameter data may be obtained before, during, and/or after adjustment of a gastric band, and may be useful for adjustment, diagnostic, monitoring, or other purposes, and may also be obtained with respect to a mechanically actuated gastric band. In settings where a fluid-filled gastric band is used, pressure data may be used to determine whether the amount of fluid in the gastric band needs to be adjusted; and/or for other purposes.

While a variety of gastric band systems have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1:
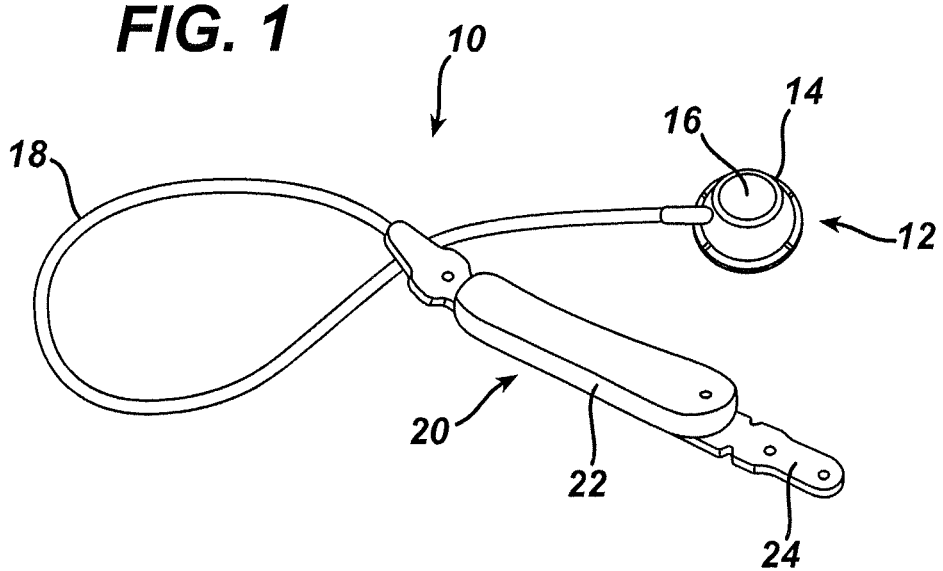
FIG. 1 depicts a perspective view of an implantable portion of an exemplary gastric band system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Gastric Band System Overview

FIGS. 1-4 illustrate an exemplary gastric band system (10). As shown, gastric band system (10) comprises an injection port (12), a gastric band (20), and a catheter (18). Injection port (12) of the present example comprises a port housing (14) and a needle penetrable septum (16). Port housing (14) defines a fluid reservoir (not shown), such that a needle may pierce septum (16) to reach the reservoir and add or withdraw fluid (e.g., saline, etc.) as described in greater detail below. Port housing (14) may be formed of titanium, plastic, or any other suitable material or combination of materials. Septum (16) may be formed of silicone or any other suitable material or combination of materials. Injection port (12) may be subcutaneously secured over a patient's sternum, to the patient's abdominal fascia, or in any other suitable location. In some versions, injection port (12) is configured and operable in accordance with the teachings of U.S. Pub. No. 2005/0283118, entitled "Implantable Medical Device with Simultaneous Attachment Mechanism and Method," published Dec. 22, 2005, and issued Dec. 14, 2010 as U.S. Pat. No. 7,850,660, the disclosure of which is incorporated by reference herein. Alternatively, injection port (12) may have any other suitable configuration and/or operability.

Gastric band (20) of the present example comprises an inflatable bladder (22) that is secured to a flexible strap (24). Inflatable bladder (22) may be formed of silicone or any other suitable material or combination of materials. Catheter (18) provides fluid communication between bladder (22) and the reservoir of injection port (12). Accordingly, a needle that is inserted through septum (16) may be used to add or withdraw fluid from inflatable bladder (22), to adjust the restriction created by gastric band (20) as described in greater detail below. In some versions, gastric band (20) is configured and operable in accordance with the teachings of U.S. Pat. No. 7,416,528, entitled "Latching Device for Gastric Band," issued Aug. 26, 2008, the disclosure of which is incorporated by reference herein. Alternatively, gastric band (20) may have any other suitable configuration and/or operability.

Figure 2:
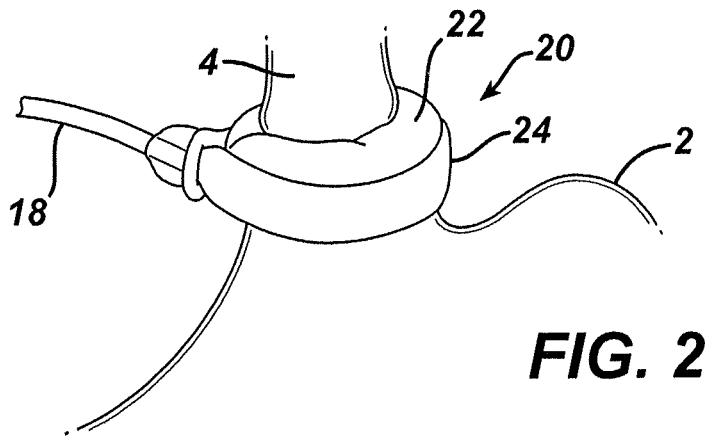
FIG. 2 depicts a perspective view of the gastric band of FIG. 1, showing the band positioned around the gastro-esophageal junction of a patient.

In some settings, gastric band (20) is applied about the gastro-esophageal junction of a patient. In particular, and as shown in FIG. 2, gastric band (20) is installed such that bladder (22) is adjacent to the tissue of the gastro-esophageal junction, with strap (24) on the outside of bladder (22). The ends of strap (24) are secured relative to each other when gastric band (20) is sufficiently wrapped about the patient's stomach (2). While strap (24) is flexible in this example, strap (24) substantially resists stretching along its length. Accordingly, when fluid is added to bladder (22) (e.g., using a needle inserted through septum (16) of injection port (12), etc.), bladder (22) expands and exerts inward forces on the gastro-esophageal junction of the patient. This reduces the size of the internal stoma at the gastro-esophageal junction, thereby creating a restriction on food intake into the patient's stomach (2). It should be understood that the size of this stoma may be decreased by adding more fluid to bladder (22) to create a greater degree of restriction; or increased by withdrawing fluid from bladder (22) to reduce the degree of restriction.

Figure 3:
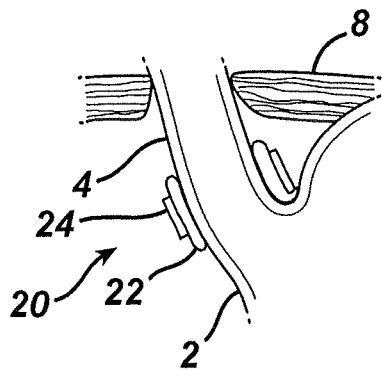
FIG. 3 depicts a cross-sectional view of the gastric band of FIG. 1, showing the band positioned around the gastro-esophageal junction of a patient in a deflated configuration.
Figure 4:
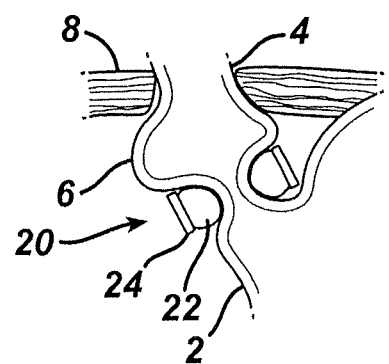
FIG. 4 depicts a cross-sectional view of the gastric band of FIG. 1, showing the band positioned around the gastro-esophageal junction of a patient in an inflated configuration to create a food intake restriction.

As shown in FIGS. 2-4, an installed gastric band (20) at least substantially encloses the upper portion of stomach (2) near the junction with esophagus (4) in the present example. FIG. 3 shows gastric band (20) in a deflated configuration, where bladder (22) contains little to no fluid, thereby maximizing the size of the stoma opening into stomach (2). FIG. 4 shows gastric band (20) in an inflated, fluid-filled configuration, where bladder (22) contains substantially more fluid than is shown in FIG. 3. In this configuration shown in FIG. 4, the pressure of gastric band (20) against stomach (2) is increased due to the fluid within bladder (22), thereby decreasing the stoma opening to create a food intake restriction. FIG. 4 also schematically illustrates the dilation of esophagus (4) above gastric band (20) to form an upper pouch (6) beneath the diaphragm muscle (8) of the patient.

II. Exemplary Catheter Protection and/or Retention Features

In some versions of gastric band system (10), factors such as the method of installation of gastric band system (10) in a patient (e.g., improper installation) may present complication risks associated with catheter (18). For instance, in some versions, catheter (18) may become inadvertently disconnected from injection port (12) after gastric band system (10) has been installed in a patient. With gastric band system (10) being a closed fluid circuit, such disconnection may result in loss of fluid pressure in bladder (22), resulting in failure of gastric band system (10) in some versions. In addition or in the alternative, catheter (18) may be oriented such that a kink forms in catheter (18) (e.g., at or near the junction of catheter (18) and injection port (12), etc.), which may result in restriction of the flow of fluid between injection port (12) and bladder (22), the flow of fluid between injection port (12) and bladder (22) being essentially cut off entirely, and/or other results. Furthermore, as noted above, in some instances a syringe may be used to adjust the level of fluid in gastric band system (10) after gastric band system (10) is implanted in a patient, by percutaneously inserting the needle (e.g., Huber needle) of the syringe through septum (16) then adding or withdrawing fluid with the syringe to adjust the degree of restriction caused by gastric band (20). There may be risks in some instances where the needle of the syringe misses septum (16) and instead pierces catheter (18), particularly in settings where the implantation of gastric band system (10) is complete and the physician is unable to fully visualize injection port (12). Thus, in some versions and/or installations of gastric band system (10), it may be desirable to reduce the likelihood (if not prevent) the inadvertent disconnection of catheter (18) from injection port (12), kinking in catheter (18), and/or inadvertent penetration of catheter (18) with a needle. Several examples of ways in which one or more of such situations may be substantially avoided will be described in greater detail below, while several other suitable examples will be apparent to those of ordinary skill in the art in view of the teachings herein.

A. Exemplary Catheter Anchor

Figure 5:
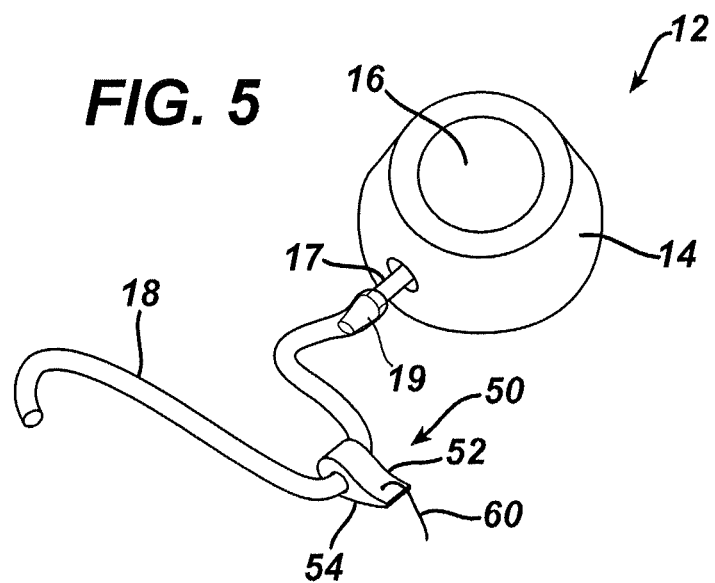
FIG. 5 depicts a perspective view of an exemplary injection port with a catheter anchor, suitable for use with the gastric band system of FIG. 1.

FIG. 5 shows an example of an anchor (50) that may be used to secure a catheter (18) to tissue. In this example, catheter (18) is coupled with an injection port (12) as described above. In particular, catheter (18) is coupled with a connector (17), which has a barbed tip (19) to substantially resist inadvertent decoupling of catheter (18), and which is in fluid communication with the reservoir of injection port (12). In some versions, connector (17) is configured to pivot relative to housing (14) (e.g., through a conical range of motion, etc.) while still providing fluid communication with the reservoir of injection port (12) without leaking at a pivot joint. Various suitable ways in which such pivotability may be provided (e.g., ball and socket joint, etc.) will be apparent to those of ordinary skill in the art in view of the teachings herein. In addition or in the alternative, connector (17) may be collapsible (e.g., like an accordion and/or telescope, etc.).

Anchor (50) of this example comprises a single folded piece of material forming a pair of apposed leaves (52, 54). Catheter (18) is positioned between leaves (52, 54). Leaves (52, 54) are secured to tissue by a suture (60) in the present example, though it should be understood that leaves (52, 54) may be secured to tissue by a staple, tack, adhesive, and/or using any other suitable devices or techniques. It should also be understood that anchor (50) may include one or more structural features configured to promote in-growth of tissue on and/or around anchor (50), such that anchor (50) may eventually be substantially held in place by tissue. In some such versions, suture (60) or some other structure that is used to initially secure anchor (50) to tissue may be made of a bioabsorbable/biodegradable material, such that the suture (60) or other structure substantially disappears after in-grown/overgrown tissue has secured anchor (50) to adjacent tissue. By way of example only, such in-growth features may be provided in and/or on anchor (50) in accordance with any of the teachings of U.S. patent application Ser. No. 12/946,923, entitled "Implantable Injection Port with Tissue In-Growth Promoter," filed on even date herewith, and published May 17, 2012 as U.S. Pub. No. 2012/0123197, the disclosure of which is incorporated by reference herein. Various other suitable ways in which in-growth features may be provided in and/or on anchor (50) will be apparent to those of ordinary skill in the art in view of the teachings herein.

As another merely illustrative example, anchor (50) may be tethered to injection port (12) via a flexible member such as a polypropylene mesh, a plastic strap, a silicone strap, etc. The length of such a tether (not shown) may be selected such that it is shorter than the length of catheter (18) that is between injection port (12) and anchor (50). In some such examples, tensile loads and/or generally transverse loads that are applied to catheter (18) may be transferred from anchor (50) to port (12) via the tether and/or from anchor (50) to the tissue to which anchor (50) is secured; instead of being transferred to the interface of catheter (18) and port connector (17). Such transference of load may reduce the possibility of catheter (18) being inadvertently disconnected from connector (17). It should also be understood that, in some versions where anchor (50) is tethered to port (12), anchor (50) need not necessarily be secured directly to tissue at all.

In some versions, when anchor (50) is secured to catheter (18), friction between leaves (52, 54) and catheter (18) is sufficient to substantially resist sliding of catheter (18) through anchor (50). In other words, friction between leaves (52, 54) and catheter (18) may keep the length of catheter (18) extending between connector (17) and anchor (50) substantially consistent. In addition or in the alternative, anchor (50) may include one or more features that allow catheter (18) to slide in one direction relative to anchor (50) while substantially preventing catheter (18) from sliding in an opposite direction relative to anchor (50). Various suitable ways in which such features may be provided (e.g., distally oriented barbs, etc.) will be apparent to those of ordinary skill in the art in view of the teachings herein. In some other versions, anchor (50) may be configured such that catheter (18) is allowed to slide freely through anchor (50), even after anchor (50) is secured to tissue. Anchor (50) may nevertheless still anchor catheter (18) to tissue, restricting movement of catheter (18) in directions transverse to the longitudinal axis of catheter (18).

In an exemplary use, gastric band (20) and injection port (12) are first installed in a patient. Then catheter (18) is secured to gastric band (20) and injection port (12). Next, anchor (50) is secured to catheter (18) by placing the strip of material forming anchor (50) next to catheter (18), bending the strip of material to wrap around catheter (18) and to form leaves (52, 54), and then leaves (52, 54) are secured to tissue (e.g., abdominal fascia, etc.) by suture (60). As another variation, anchor (50) may be bent to form leaves (52, 54), then leaves (52, 54) may be secured to tissue by suture (60), and then catheter (18) may be fed through the opening formed between bent leaves (52, 54) before catheter (18) is secured to gastric band (20) and/or injection port (12). It should also be understood that anchor (50) may be resiliently biased to assume a bent configuration with leaves (52, 54) in an apposed configuration. Such versions of anchor (50) may nevertheless have enough flexibility to allow leaves (52, 54) to be spread apart to allow catheter (18) to be inserted between leaves (52, 54) at an appropriate time. As yet another merely illustrative variation, anchor (50) may include a living hinge separating leaves (52, 54), and may fold open to accept catheter (18) between leaves (52, 54) and then fold closed around catheter (18), with a snap fitting to substantially lock leaves (52, 54) together. Other suitable ways in which anchor (50) may be used will be apparent to those of ordinary skill in the art in view of the teachings herein.

In some other versions, anchor (50) is not a preformed piece of material that is bent to form leaves (52, 54). For instance, anchor (50) may comprise a single piece of plastic that is molded to the shape shown in FIG. 5 or some other shape. Such a single piece may define an opening through which catheter (18) may be inserted. Such a single piece may also be secured to tissue by a suture (60), staple, tack, adhesive, etc. Various other suitable components, features, and configurations for anchor (50) will be apparent to those of ordinary skill in the art in view of the teachings herein. It should also be understood that, while a single anchor (50) is shown in FIG. 5, any suitable number of anchors (50) may be used to anchor catheter (18) to tissue at various locations along the length of catheter (18). Furthermore, it should be understood that anchor (50) may be used in conjunction with any of the injection ports shown in FIGS. 6-15, any other injection ports, or any other settings in which a catheter (18) or similar component is used.

B. Exemplary Catheter Retention Recess

Figure 6:
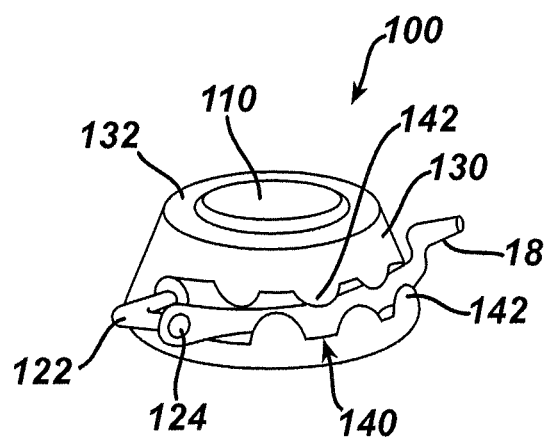
FIG. 6 depicts a perspective view of another exemplary injection port with a catheter retention and protection feature, suitable for use with the gastric band system of FIG. 1.
Figure 7:
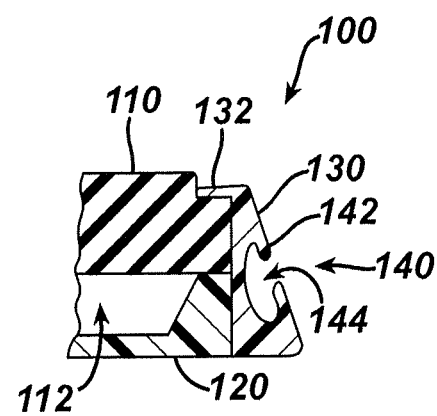
FIG. 7 depicts an enlarged, cross-sectional view of a portion of the injection port of FIG. 6.

FIGS. 6-7 show an exemplary alternative injection port (100). Injection port (100) of this example includes a septum (110), a base (120), and an outer body (130). Septum (110) is sandwiched between base (120) and outer body (130), and is configured to self-seal when penetrated by a needle (e.g., a Huber needle). Septum (110) and base (120) together define a fluid reservoir (112). Outer body (130) includes an inwardly extending lip (132) defining an opening having a diameter that is less than the outer diameter of septum (110). Outer body (130) is secured to base (120), such that septum (110), base (120), and outer body (130) form a unitary construction. Base (120) comprises a connector (122), which extends radially outwardly through outer body (130) then tangentially relative to base (120) to form a substantially right angle in this example. Of course, one of ordinary skill in the art will immediately recognize that this configuration of connector (122) is just one merely illustrative example, and that connector (122) may alternatively have any other suitable configuration, including but not limited to being substantially straight, curved, bent at a non-right angle, provided in a pivoting relationship with base (120), etc. Connector (122) of the present example is in fluid communication with reservoir (112), and includes a barbed tip (124). A catheter (18) is coupled with connector (122), such that fluid may be communicated between reservoir (112) and a gastric band (20) at the other end of catheter (18) via connector (122) and catheter (18).

Outer body (130) of this example includes a catheter retention feature (140) about part of its outer periphery. Catheter retention feature (140) comprises a plurality of rounded tabs (142) extending about a recess (144). Recess (144) is configured to receive catheter (18), and tabs (142) are configured to substantially retain catheter (18) in recess. In some versions, tabs (142) and recess (144) are configured such that catheter (18) must be compressed or otherwise be deformed in order to be fit into recess (144); and also such that catheter (18) remains compressed or otherwise deformed within recess (144). Such compression or deformation, along with elastomeric properties of catheter (18), may provide friction that substantially resists longitudinal and/or transverse sliding of catheter (18) in recess (144). However, such compression or deformation of catheter (18) does not significantly restrict the flow of fluid through catheter (18). In the present example, tabs (142) are provided in an alternating arrangement along the top and bottom of recess (144). Of course, tabs (142) may be provided in any other suitable arrangement. In addition, while tabs (142) have substantially semicircular shapes in the present example, tabs (142) may alternatively have any other suitable shapes. Catheter retention feature (140) may extend along the perimeter of outer body (130) to any suitable extent. In some versions, catheter retention feature (140) extends along at least 90° of the 360° perimeter of outer body (130), though it should be understood that catheter retention feature (140) may extend along the perimeter of outer body (130) to any other suitable extent.

In the present example, the configuration and location of catheter retention feature (140) may substantially reduce the likelihood that catheter (18) will be disconnected from connector (122) after injection port (100) has been implanted in a patient. For instance, by wrapping catheter (18) around a substantial portion of the perimeter of outer body (130), catheter retention feature (140) may provide a substantial increase in retention force due to the relatively large amount of contact surface area between catheter (18) and outer body (130) and the phenomenon of increasing normal force (and therefore friction forces) as catheter (18) is pulled relative to injection port (100). In addition, the configuration of catheter retention feature (140), as well as the bent configuration of connector (122), may substantially reduce the likelihood that catheter (18) will become kinked near injection port (100) after injection port (100) has been implanted in a patient. Furthermore, catheter retention feature (140) may provide a shield for catheter (18), substantially reducing the likelihood that a needle aiming for septum (110) will inadvertently penetrate catheter (18) when the user misses septum (110) with the needle after injection port (100) has been implanted in a patient. Alternatively, catheter retention feature (140) may provide other results, in addition to or in lieu of any or all of those described above.

In some exemplary uses, catheter (18) is inserted in recess (144) by first inserting a free end of catheter (18) into one end of recess (144), then sliding catheter (18) along the circumferential length of recess (144) until the free end of catheter (18) reaches the other end of recess (144). This may be done from the end of recess (144) that is nearest connector (122) or from the other end of recess (144). In some other exemplary uses, catheter (18) is inserted in recess (144) by squeezing catheter between tabs (142) along a path that is substantially radially inward relative to the center of injection port (180). In either case, catheter (18) may be coupled with connector (122) before or after catheter (18) is inserted in recess (144). Various other suitable configurations that catheter retention feature (140) may have will be apparent to those of ordinary skill in the art in view of the teachings herein. Similarly, various other suitable ways in which catheter retention feature (140) may be used will be apparent to those of ordinary skill in the art in view of the teachings herein.

C. Exemplary Catheter Retention Sleeve

Figure 8:
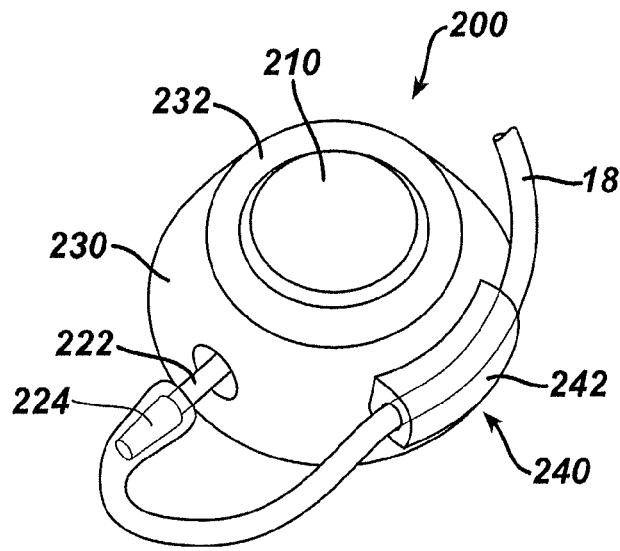
FIG. 8 depicts a perspective view of another exemplary injection port with a catheter retention and protection feature, suitable for use with the gastric band system of FIG. 1.
Figure 9:
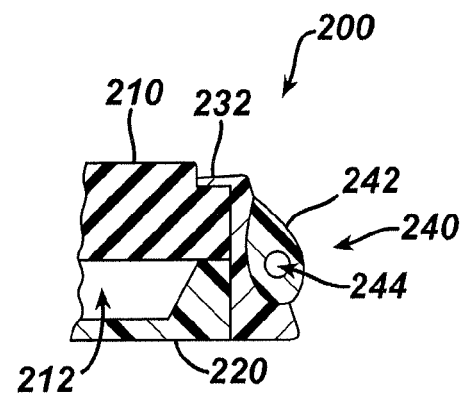
FIG. 9 depicts an enlarged, cross-sectional view of a portion of the injection port of FIG. 8.

FIGS. 8-9 show another exemplary alternative injection port (200). Injection port (200) of this example includes a septum (210), a base (220), and an outer body (230). Septum (210) is sandwiched between base (220) and outer body (230), and is configured to self-seal when penetrated by a needle (e.g., a Huber needle). Septum (210) and base (220) together define a fluid reservoir (212). Outer body (230) includes an inwardly extending lip (232) defining an opening having a diameter that is less than the outer diameter of septum (210). Outer body (230) is secured to base (220), such that septum (210), base (220), and outer body (230) form a unitary construction. Base (220) comprises a connector (222), which is in fluid communication with reservoir (212), extends through outer body (230), and includes a barbed tip (224). Of course, as with any other connector described herein, the tip of connector (222) need not necessarily be barbed. Indeed, it is contemplated that the tip of every connector referred to herein may have any suitable configuration, including but not limited to barbed configurations and non-barbed configurations. Connector (222) of the present example is substantially straight, though it should be understood that connector (222) may instead extend radially outwardly through outer body (230) then tangentially relative to base (220) to form a substantially right angle, similar to connector (122) described above and shown in FIG. 6. Of course, connector (222) may have any other suitable configuration. A catheter (18) is coupled with connector (222), such that fluid may be communicated between reservoir (212) and a gastric band (20) at the other end of catheter (18) via connector (222) and catheter (18).

Outer body (230) of this example includes a catheter retention feature (240) about part of its outer periphery. Catheter retention feature (240) of this example includes a sleeve (242). Sleeve (242) is secured to the side of outer body (230) and defines a channel (244). In the present example, sleeve (242) is formed as a separate component that is secured to outer body (230) by an adhesive, though it should be understood that sleeve (242) may be provided in any other suitable fashion. By way of example only, sleeve (242) may be molded together as an integral feature of outer body (230), such that sleeve (242) and outer body (230) form a homogenous continuum of material. Channel (244) is configured to receive catheter (18), and sleeve (242) is configured to substantially retain catheter (18) in channel (244). In some versions, channel (244) has an inner diameter that is slightly less than the outer diameter of catheter (18), such that catheter (18) must be compressed in order to fit in channel (244); and also such that catheter (18) remains compressed within channel (244). Such compression, along with elastomeric properties of catheter (18), may provide friction that substantially resists longitudinal and/or transverse sliding of catheter (18) in channel (244). However, such compression or deformation of catheter (18) does not significantly restrict the flow of fluid through catheter (18). In addition or in the alternative, channel (244) may include one or more features that allow catheter (18) to slide in one direction through channel (244) while substantially preventing catheter (18) from sliding in an opposite direction through channel (244). Various suitable ways in which such features may be provided (e.g., proximally oriented barbs, etc.) will be apparent to those of ordinary skill in the art in view of the teachings herein. In some other versions, channel (244) may be configured such that catheter (18) is allowed to slide freely through channel (244).

In the present example, the configuration and location of catheter retention feature (240) may substantially reduce the likelihood that catheter (18) will be disconnected from connector (222) after injection port (200) has been implanted in a patient. In addition, the configuration of catheter retention feature (240) may substantially reduce the likelihood that catheter (18) will become kinked near injection port (200) after injection port (200) has been implanted in a patient. Furthermore, catheter retention feature (240) may provide a shield for catheter (18), substantially reducing the likelihood that a needle aiming for septum (210) will inadvertently penetrate catheter (18) when the user misses septum (210) with the needle after injection port (200) has been implanted in a patient. Alternatively, catheter retention feature (240) may provide other results, in addition to or in lieu of any or all of those described above.

In some exemplary uses, catheter (18) is inserted in channel (244) by first inserting a free end of catheter (18) into one end of channel (244), then sliding catheter (18) along the circumferential length of channel (244) until the free end of catheter (18) reaches the other end of channel (244). This may be done from the end of channel (244) that is nearest connector (222) or from the other end of channel (244). Catheter (18) may be coupled with connector (222) before or after catheter (18) is inserted in channel (244). Of course, in some versions where catheter (18) is integral or unitary with gastric band (20), it may not be possible to couple catheter (18) with connector (222) before inserting catheter (18) in channel (244). Various other suitable configurations that catheter retention feature (240) may have will be apparent to those of ordinary skill in the art in view of the teachings herein. Similarly, various other suitable ways in which catheter retention feature (240) may be used will be apparent to those of ordinary skill in the art in view of the teachings herein.

D. Exemplary Catheter Retention Tab

Figure 10:
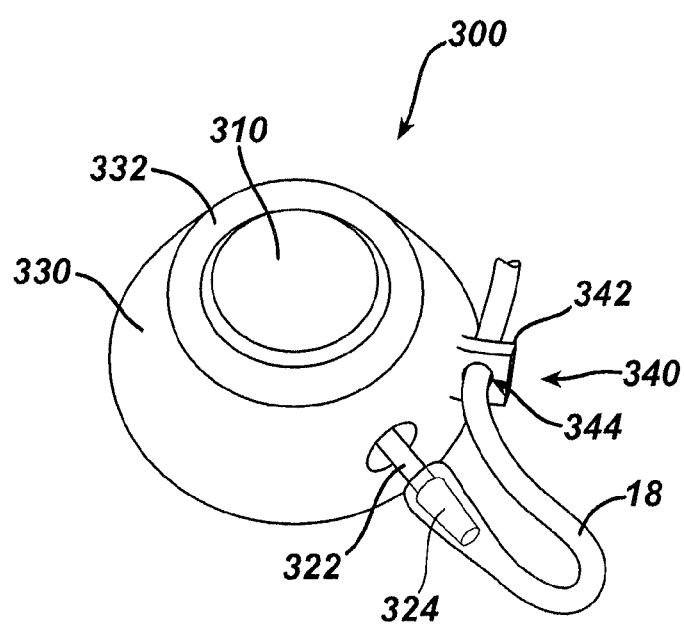
FIG. 10 depicts a perspective view of another exemplary injection port with a catheter retention feature, suitable for use with the gastric band system of FIG. 1.
Figure 11:
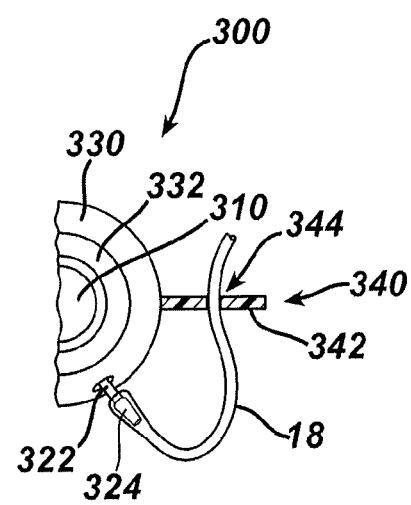
FIG. 11 depicts an enlarged view of a portion of the injection port of FIG. 10, with a catheter retention feature shown in cross-section.

FIGS. 10-11 show another exemplary alternative injection port (300). Injection port (300) of this example includes a septum (310), a base (not shown), and an outer body (330). Septum (310) is sandwiched between the base and outer body (330), and is configured to self-seal when penetrated by a needle (e.g., a Huber needle). Septum (310) and the base together define a fluid reservoir (not shown). Outer body (330) includes an inwardly extending lip (332) defining an opening having a diameter that is less than the outer diameter of septum (310). Outer body (330) is secured to the base, such that septum (310), the base, and outer body (330) form a unitary construction. The base comprises a connector, which is in fluid communication with the reservoir, extends through outer body (330), and includes a barbed tip (324). Connector (322) of this example is substantially straight, though it should be understood that connector (322) may instead extend radially outwardly through outer body (330) then tangentially relative to the base to form a substantially right angle, similar to connector (122) described above and shown in FIG. 6. Of course, connector (322) may have any other suitable configuration. A catheter (18) is coupled with connector (322), such that fluid may be communicated between the reservoir of injection port (300) and a gastric band (20) at the other end of catheter (18) via connector (322) and catheter (18).

Outer body (330) of this example includes a catheter retention feature (340) positioned on its outer periphery. Catheter retention feature (340) of this example includes a tab (342). Tab (342) extends outwardly from the side of outer body (330) and defines an opening (344). In the present example, tab (342) is molded as an integral feature of outer body (330), such that tab (342) and outer body (330) form a homogenous continuum of material. In some other versions, tab (342) is initially provided as a separate component that is secured to outer body (330) by an adhesive or other suitable means, though it should be understood that tab (342) may be provided in any other suitable fashion. Opening (344) is configured to receive catheter (18), and tab (342) is configured to substantially retain catheter (18) in opening (344). In some versions, opening (344) has an inner diameter that is slightly less than the outer diameter of catheter (18), such that catheter (18) must be compressed in order to fit in opening (344); and also such that catheter (18) remains compressed within opening (344). Such compression, along with elastomeric properties of catheter (18), may provide friction that substantially resists longitudinal and/or transverse sliding of catheter (18) in opening (344). However, such compression or deformation of catheter (18) does not significantly restrict the flow of fluid through catheter (18).

In the present example, the configuration and location of catheter retention feature (340) may substantially reduce the likelihood that catheter (18) will be disconnected from connector (322) after injection port (300) has been implanted in a patient. In addition, the configuration of catheter retention feature (340) may substantially reduce the likelihood that catheter (18) will become kinked near injection port (300) after injection port (300) has been implanted in a patient. Alternatively, catheter retention feature (340) may provide other results, in addition to or in lieu of any or all of those described above. It should be understood that catheter (18) may be coupled with connector (322) before or after catheter (18) is inserted in opening (344). Of course, in some versions where catheter (18) is integral or unitary with gastric band (20), it may not be possible to couple catheter (18) with connector (322) before inserting catheter (18) in opening (344). Various other suitable configurations that catheter retention feature (340) may have will be apparent to those of ordinary skill in the art in view of the teachings herein. Similarly, various other suitable ways in which catheter retention feature (340) may be used will be apparent to those of ordinary skill in the art in view of the teachings herein.

E. Exemplary Catheter Protection Recess

Figure 12:
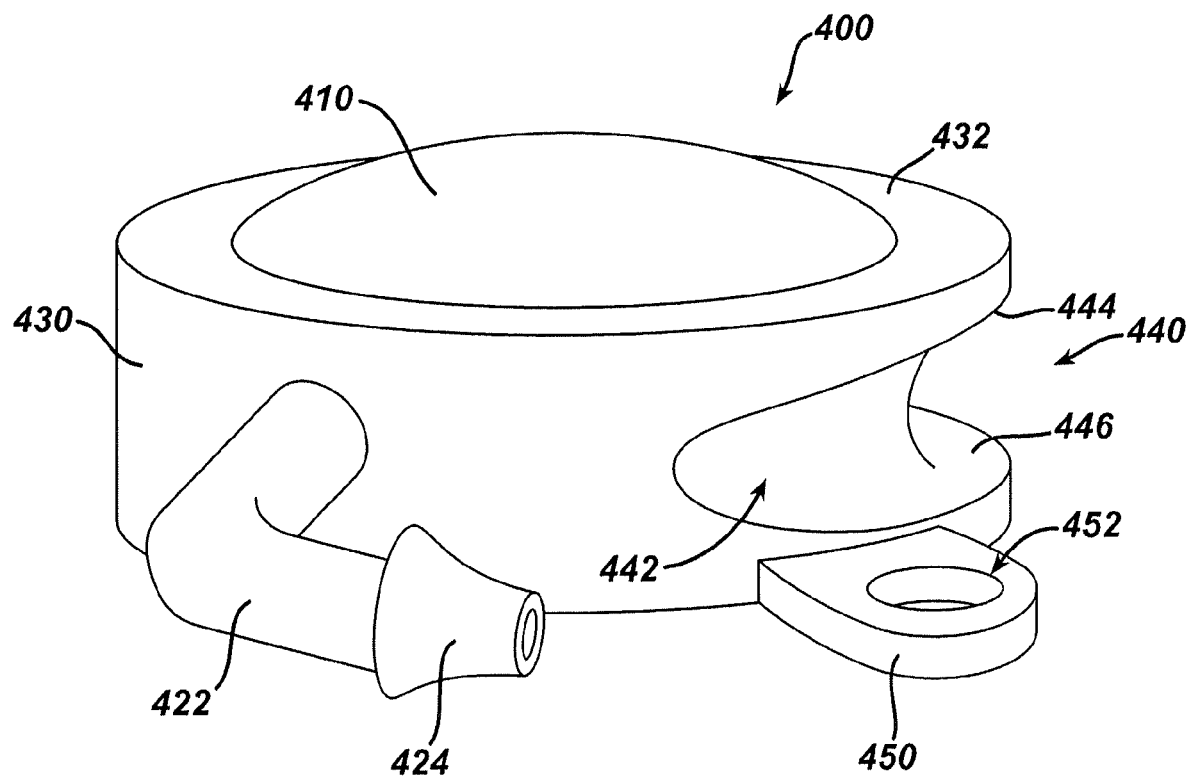
FIG. 12 depicts a perspective view of another exemplary injection port with a catheter protection feature, suitable for use with the gastric band system of FIG. 1.
Figure 13:
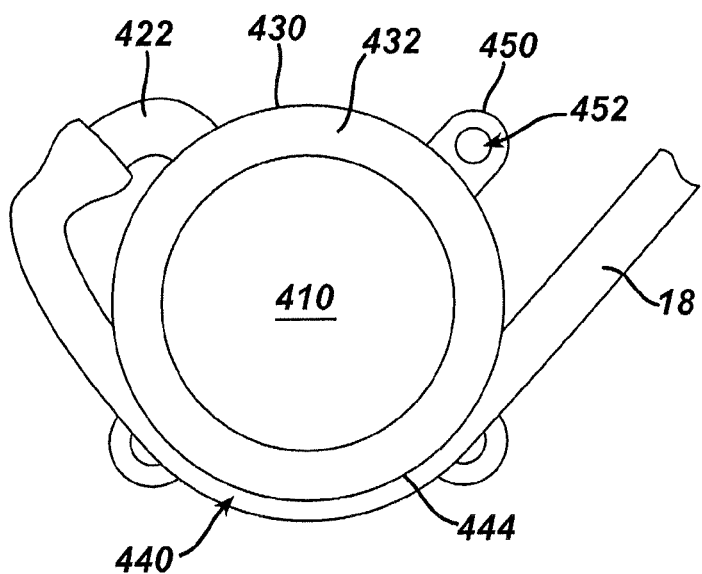
FIG. 13 depicts a top plan view of the injection port of FIG. 12.

FIGS. 12-13 show another exemplary alternative injection port (400). Injection port (400) of this example includes a septum (410), a base (not shown), and an outer body (430). Septum (410) is sandwiched between the base and outer body (430), and is configured to self-seal when penetrated by a needle (e.g., a Huber needle). Septum (410) and the base together define a fluid reservoir (not shown). Outer body (430) includes an inwardly extending lip (432) defining an opening having a diameter that is less than the outer diameter of septum (410). Outer body (430) is secured to the base, such that septum (410), the base, and outer body (430) form a unitary construction. The base comprises a connector (422), which extends radially outwardly through outer body (430) then tangentially relative to the base to form a substantially right angle. Connector (422) is in fluid communication with the reservoir, and includes a barbed tip (424). A catheter (18) is coupled with connector (422), such that fluid may be communicated between the reservoir and a gastric band (20) at the other end of catheter (18) via connector (422) and catheter (18).

Outer body (430) of this example includes a catheter protection feature (440) about part of its outer periphery. Catheter protection feature (440) comprises a circumferentially extending recess (442) defined between an upper shelf (444) and a lower shelf (446). Recess (442) is configured to receive at least part of catheter (18). In the example shown in FIG. 13, part of catheter (18) is exposed relative to shelves (444, 446), though it should be understood that recess (442) may be configured such that catheter is not exposed relative to shelves (444, 446). Also in the present example, no other components are configured to retain catheter (18) in recess (442). Instead, when injection port (400) is installed in a patient, injection port (400) is rotated to position connector (422) at an angular position where catheter (18) will simply be wrapped about at least part of the exterior of outer body (430) to reach gastric band (20). Of course, a variety of features and techniques may be used to substantially keep catheter (18) in recess (442). For instance, clips, tabs, or other retention features may be incorporated into upper shelf (444) and/or lower shelf (446). In addition or in the alternative, an anchor (50) may be used to maintain tension in at least part of catheter (18) near injection port (400). As yet another merely illustrative example, an adhesive may be used to secure catheter (18) in recess (442). It should also be understood that recess (442) may be sized to provide at least a slight interference fit with catheter (18), such that catheter (18) is essentially gripped by shelves (444, 446) when catheter (18) is disposed in recess (442). Catheter protection feature (440) may extend along the perimeter of outer body (430) to any suitable extent. In some versions, catheter protection feature (440) extends along at least 90° of the 360° perimeter of outer body (430), though it should be understood that catheter protection feature (440) may extend along the perimeter of outer body (430) to any other suitable extent.

In the present example, the configuration and location of catheter protection feature (440) may substantially reduce the likelihood that catheter (18) will be disconnected from connector (422) after injection port (400) has been implanted in a patient. For instance, by wrapping catheter (18) around a substantial portion of the perimeter of outer body (430) and/or by providing an interference fit for catheter (18) in recess (442), catheter protection feature (440) may provide a substantial increase in retention force due to the relatively large amount of contact surface area between catheter (18) and outer body (430) and the phenomenon of increasing normal force (and therefore friction forces) as catheter (18) is pulled relative to injection port (400). In addition, the configuration and location of catheter protection feature (440), as well as the bent configuration of connector (422), may substantially reduce the likelihood that catheter (18) will become kinked near injection port (400) after injection port (400) has been implanted in a patient. Furthermore, catheter protection feature (440) may provide a shield for catheter (18), substantially reducing the likelihood that a needle aiming for septum (410) will inadvertently penetrate catheter (18) when the user misses septum (410) with the needle after injection port (400) has been implanted in a patient. Alternatively, catheter protection feature (440) may provide other results, in addition to or in lieu of any or all of those described above. Various other suitable configurations that catheter protection feature (440) may have will be apparent to those of ordinary skill in the art in view of the teachings herein. Similarly, various other suitable ways in which catheter protection feature (440) may be used will be apparent to those of ordinary skill in the art in view of the teachings herein.

Injection port (400) of the present example also includes anchor tabs (450). Each anchor tab (450) is a unitary feature of outer body (430) in the present example, though it should be understood that one or all of anchor tabs (450) may instead be a unitary feature of the base of injection port (400). Each anchor tab (450) defines a respective opening (452) that may receive a suture, staple, tack, etc., to secure injection port (400) to tissue. Of course, injection port (400) may be secured to tissue in any other suitable fashion. By way of example only, and as with any other injection port described herein, injection port (400) may include integral fasteners and/or any other features as taught in U.S. Pub. No. 2005/0283118, issued as U.S. Pat. No. 7,850,660, the disclosure of which is incorporated by reference herein.

F. Exemplary Catheter Protection Bell

Figure 14:
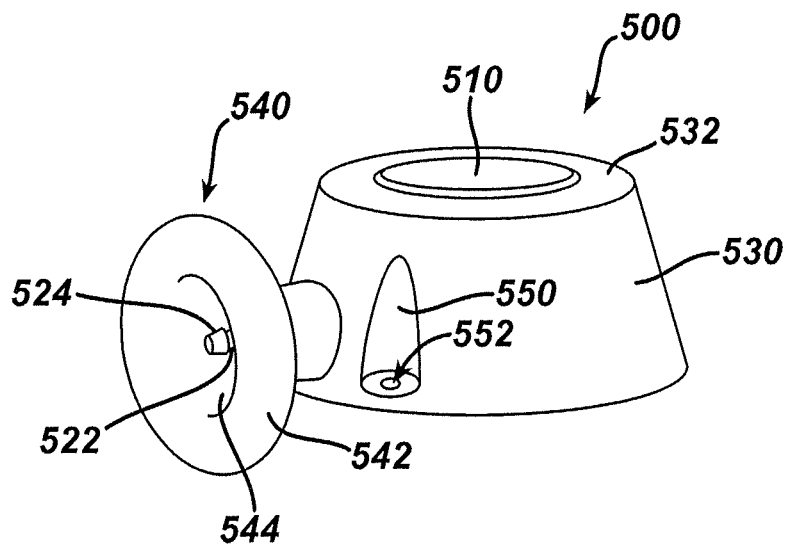
FIG. 14 depicts a perspective view of another exemplary injection port with a catheter protection feature, suitable for use with the gastric band system of FIG. 1.
Figure 15:
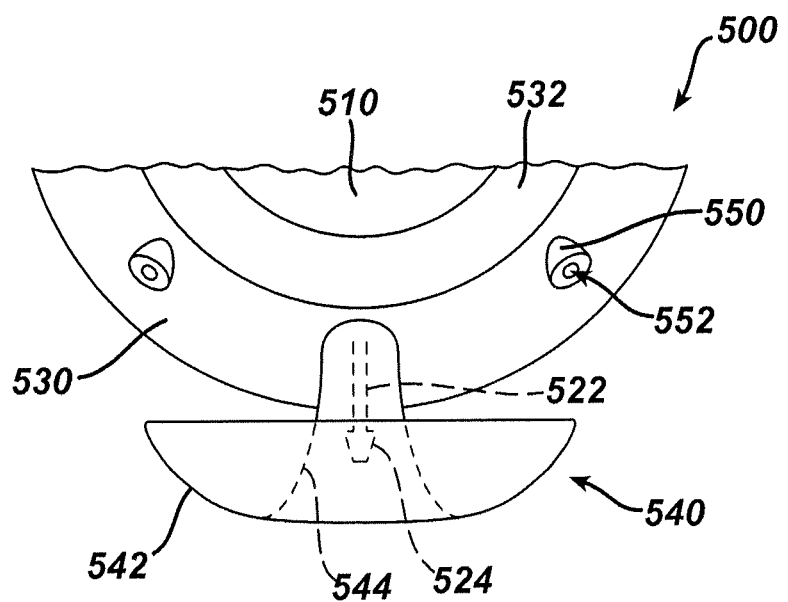
FIG. 15 depicts an enlarged partial view of the injection port of FIG. 14.

FIGS. 14-15 show another exemplary alternative injection port (500). Injection port (500) of this example includes a septum (510), a base (not shown), and an outer body (530). Septum (510) is sandwiched between the base and outer body (530), and is configured to self-seal when penetrated by a needle (e.g., a Huber needle). Septum (510) and the base together define a fluid reservoir (not shown). Outer body (530) includes an inwardly extending lip (532) defining an opening having a diameter that is less than the outer diameter of septum (510). Outer body (530) is secured to the base, such that septum (510), the base, and outer body (530) form a unitary construction. The base comprises a connector (522), which extends radially outwardly through outer body (530) then tangentially relative to the base to form a substantially right angle. Connector (522) is in fluid communication with the reservoir, and includes a barbed tip (524). A catheter (18) may be coupled with connector (522), such that fluid may be communicated between the reservoir and a gastric band (20) at the other end of catheter (18) via connector (522) and catheter (18).

Outer body (530) of this example includes a catheter protection feature (540) surrounding connector (522). Catheter protection feature (540) comprises a bell-shaped feature including an outwardly and rearwardly extending rim (542). As best seen in FIG. 15, rim (542) is generally convexly curved in the present example, though it should be understood that rim (542) may alternatively have any other suitable configuration. In addition, the interior surface (544) of catheter protection feature (540) is generally convexly curved in the present example, funneling toward connector (522), though it should be understood that interior surface (544) may have any other suitable configuration. Connector (522) is substantially centered and coaxially aligned relative to catheter protection feature (540).

In the present example, the configuration and location of catheter protection feature (540) may substantially reduce the likelihood that catheter (18) will become kinked near injection port (500) after injection port (500) has been implanted in a patient. For instance, the curved configuration of rim (542) and interior surface (544) may guide catheter (18) along a curved path from connector (522) when catheter (18) is oriented generally transversely relative to connector (522) after being coupled with connector (522), rather than allowing catheter (18) to take a sharp turn that might result in kinking of catheter (18). Furthermore, catheter protection feature (540) may provide a shield for catheter (18), substantially reducing the likelihood that a needle aiming for septum (510) will inadvertently penetrate catheter (18) when the user misses septum (510) with the needle after injection port (500) has been implanted in a patient. Alternatively, catheter protection feature (540) may provide other results, in addition to or in lieu of any or all of those described above. Various other suitable configurations that catheter protection feature (540) may have will be apparent to those of ordinary skill in the art in view of the teachings herein. Similarly, various other suitable ways in which catheter protection feature (540) may be used will be apparent to those of ordinary skill in the art in view of the teachings herein.

Injection port (500) of the present example also includes anchor sinks (550). Each anchor sink (550) is recessed in outer body (530) in the present example, though it should be understood that one or all of anchor sinks (550) may instead extend outwardly from outer body (530) or have some other configuration. Each anchor sink (550) defines a respective opening (552) that may receive a suture, staple, tack, etc., to secure injection port (500) to tissue. Of course, injection port (500) may be secured to tissue in any other suitable fashion. By way of example only, and as with any other injection port described herein, injection port (500) may include integral fasteners and/or any other features as taught in U.S. Pub. No. 2005/0283118, issued as U.S. Pat. No. 7,850,660, the disclosure of which is incorporated by reference herein.

G. Exemplary Catheter Locking Connectors

Figure 16:
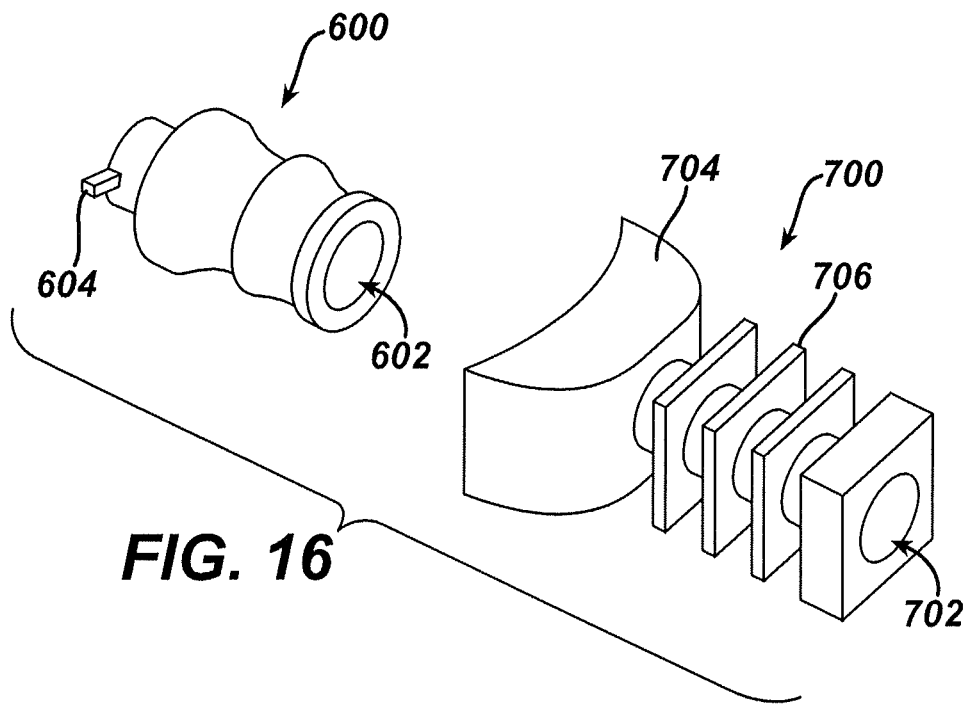
FIG. 16 depicts a perspective view of an exemplary catheter locking connector and a connector sleeve with a strain relief, suitable for use with the gastric band system of FIG. 1.

FIG. 16 shows an exemplary catheter locking connector (600) and strain relief (700) that may be used with any of the injection ports described herein, among various other types of ports. For purposes of illustration only, locking connector (600) and strain relief (700) will be described in the context of injection port (12) shown in FIGS. 1 and 5. Locking connector (600) of this example defines a channel (602) that is configured to receive catheter (18) and port connector (17). Channel (602) has an inner diameter that is slightly less than the outer diameter that is presented by catheter (18) at the widest part of barbed tip (19). Thus, when catheter (18) is secured to barbed tip (19), and then connector (600) is slid along catheter (18) until connector (600) substantially encompasses port connector (17) (including the end of catheter (18) and barbed tip (19), etc.), connector (600) substantially compresses catheter (18) against barbed tip (19). This compression further secures catheter (18) to port connector (17), substantially preventing catheter (18) from being inadvertently decoupled from port connector (17) when catheter (18) is pulled relative to injection port (12).

Connector (600) of the present example further comprises a pair of opposing outward projections (604), which are configured to be received in L-shaped or J-shaped slots (not shown) formed in housing (14) near port connector (17). In particular, the slots and projections (604) provide a bayonet fitting between connector (600) and housing (14). A user may thus slide connector (600) toward housing (14) until projections (604) reach the corresponding slots, then rotate connector (600) about the longitudinal axis defined by connector (600) until projections (604) are fully engaged with the slots. Such a bayonet fitting may substantially prevent connector (600) from being slid away from housing (14) after connector (600) has been secured in place over port connector (17) and the end of catheter (18). Of course, connector (600) and housing (14) may be secured together in any other suitable fashion, including but not limited to snap fittings, complementary threading, etc. It should also be understood that housing (14) may include an integral, outwardly extending sleeve cover (not shown) that substantially encompasses at least part of the length of connector (600).

Strain relief (700) of the present example is formed of an elastomeric material and defines a channel (702). In some versions, channel (702) is sized to receive at least a portion of connector (600). A boot portion (704) of strain relief (700) abuts housing (14) of injection port (12), and may be secured thereto by an adhesive, by being received in a slot, or in any other suitable fashion. Strain relief (700) of the present example has a length exceeding the length of the part of connector (600) protruding outwardly relative to housing (14). Thus, strain relief (700) covers part of catheter (18) that extends outwardly from connector (600). Of course, strain relief (700) may alternatively have a length that is approximately equal to the length of the part of connector (600) protruding outwardly relative to housing (14); or any other suitable length. Strain relief (700) also includes a plurality of elastomeric plate members (706) that resiliently restrict the degree to which strain relief (700) may be bent transversely. Thus, while strain relief (700) permits catheter (18) to bend, strain relief (700) provides substantial resistance to kinking (18) of catheter near injection port (12). It should be understood that this example of strain relief (700) is merely one example, and that strain relief (700) may have any other suitable components, features, or configurations. Furthermore, while connector (600) and strain relief (700) are shown as separate pieces in this example, it should be understood that connector (600) and strain relief (700) may alternatively be a single piece.

Figure 17:
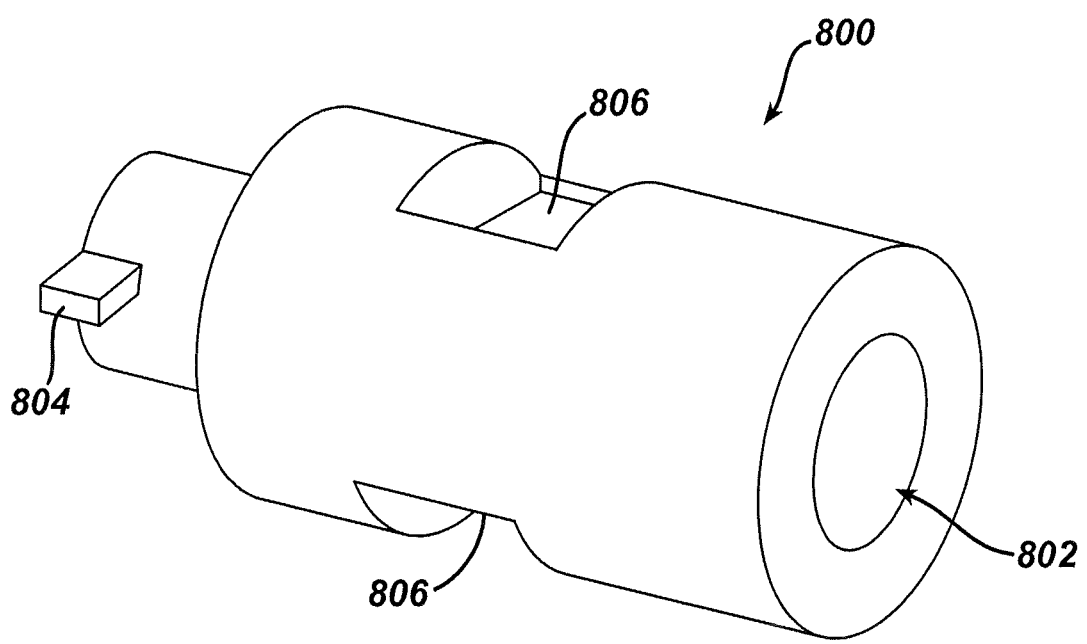
FIG. 17 depicts a perspective view of an exemplary locking connector overmold with detents for a catheter or connector sleeve with a corresponding raised material, suitable for use with the gastric band system of FIG. 1.

FIG. 17 shows another exemplary catheter locking connector (800) that may be used with any of the injection ports described herein, among various other types of ports. Again, locking connector (800) will be described in the context of injection port (12) shown in FIGS. 1 and 5 for purposes of illustration only. Like locking connector (600), locking connector (800) of this example defines a channel (802) that is configured to receive catheter (18) and port connector (17). Channel (802) has an inner diameter that is slightly less than the outer diameter that is presented by catheter (18) at the widest part of barbed tip (19). Thus, when catheter (18) is secured to barbed tip (19), and then connector (800) is slid along catheter (18) until connector (800) substantially encompasses port connector (17) (including the end of catheter (18) and barbed tip (19), etc.), connector (800) substantially compresses catheter (18) against barbed tip (19). This compression further secures catheter (18) to port connector (17), substantially preventing catheter (18) from being inadvertently decoupled from port connector (17) when catheter (18) is pulled relative to injection port (12).

Also like connector (600), connector (800) of the present example further comprises a pair of opposing outward projections (804), which are configured to be received in L-shaped or J-shaped slots (not shown) formed in housing (14) near port connector (17). In particular, the slots and projections (804) provide a bayonet fitting between connector (800) and housing (14). A user may thus slide connector (800) toward housing (14) until projections (804) reach the corresponding slots, then rotate connector (800) about the longitudinal axis defined by connector (800) until projections (804) are fully engaged with the slots. Such a bayonet fitting may substantially prevent connector (800) from being slid away from housing (14) after connector (800) has been secured in place over port connector (17) and the end of catheter (18). Of course, connector (800) and housing (14) may be secured together in any other suitable fashion, including but not limited to snap fittings, complementary threading, etc.

It should also be understood that housing (14) may include an integral, outwardly extending sleeve cover (not shown) that substantially encompasses at least part of the length of connector (800). For instance, connector (800) of the present example includes a pair of opposing lateral recesses (806). Such recesses (806) may receive corresponding protruding portions of a sleeve cover of injection port (14), providing further resistance to connector (800) being pulled off of port connector (17) and catheter (18) along a longitudinal axis defined by connector (800). Alternatively, such recesses (806) may receive corresponding protruding portions (not shown) within channel (702) of strain relief (700), providing substantial resistance to strain relief (700) being pulled off from connector (800) after strain relief (700) has been slid over and onto connector (800) or molded onto locking connector (800). It is also possible to overmold protruding portions and/or recesses onto/into catheter (18) that correspond to recesses (806), such that the overmolded portions of catheter (18) engage recesses (806) internally within channel (802) when catheter (18) is inserted into channel (802), thereby increasing resistance to catheter (18) disconnection from port connector (17). Still other suitable components, features, and configurations that may be incorporated into connector (800) will be apparent to those of ordinary skill in the art in view of the teachings herein.

III. Miscellaneous

It should be understood that the foregoing teachings may be readily applied to versions of gastric band system (10) that include an implanted pump/reservoir system (not shown) instead of including an injection port (12). Such a pump/reservoir system may be controlled to selectively vary the amount of fluid in gastric band (20). Examples of such a system are described in U.S. Pat. No. 7,390,294, entitled "Piezo Electrically Driven Bellows Infuser for Hydraulically Controlling an Adjustable Gastric Band," issued Jun. 24, 2008, the disclosure of which is incorporated by reference herein. Other examples of such a system are described in U.S. Pat. No. 7,351,240, entitled "Thermodynamically Driven Reversible Infuser Pump for Use as a Remotely Controlled Gastric Band," issued Apr. 1, 2008, the disclosure of which is incorporated by reference herein. Of course, a variety of other types of pumps and/or reservoirs may be incorporated into a gastric band system (10). Like injection port (12), such pumps and/or reservoirs may be coupled with a gastric band (20) by a catheter (18) or other type of conduit. It should therefore be understood that a pump and/or reservoir may readily include any of the catheter protection and/or retention features described above with reference to FIGS. 5-17. Similarly, an infusion port or other type of implanted device may readily include any of the catheter protection and/or retention features described above with reference to FIGS. 5-17. Various suitable ways in which the teachings herein may be applied to a pump, reservoir, and/or other type of implanted device will be apparent to those of ordinary skill in the art in view of the teachings herein.

It will also become readily apparent to those skilled in the art that examples described herein may have applicability to other types of implantable bands. For example, bands are used for the treatment of fecal incontinence. One such band is described in U.S. Pat. No. 6,461,292, entitled "Anal Incontinence Treatment with Wireless Energy Supply," issued Oct. 8, 2002, the disclosure of which is incorporated by reference herein. Bands can also be used to treat urinary incontinence. One such band is described in U.S. Pat. No. 7,621,863, entitled "Urinary Incontinence Treatment with Wireless Energy Supply," issued Nov. 24, 2009, the disclosure of which is incorporated by reference herein. Bands can also be used to treat heartburn and/or acid reflux. One such band is described in U.S. Pat. No. 6,470,892, entitled "Mechanical Heartburn and Reflux Treatment," issued Oct. 29, 2002, the disclosure of which is incorporated by reference herein. Bands can also be used to treat impotence. One such band is described in U.S. Pat. No. 7,442,165, entitled "Penile Prosthesis," issued Oct. 28, 2008, the disclosure of which is incorporated by reference herein. Various ways in which the teachings herein may be incorporated with the teachings of these patent references will be apparent to those of ordinary skill in the art.

Versions of the present invention have application in conventional endoscopic and open surgical instrumentation as well as application in robotic-assisted surgery.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
(a) a port body, wherein a sidewall of the port body defines a fluid reservoir, wherein the port body is sized and configured for implantation in a patient;
(b) a connector extending outwardly from the port body in a first direction, wherein the connector is in fluid communication with the reservoir, wherein the connector is configured to couple with a conduit for communicating fluid between the conduit and the reservoir via the connector; and
(c) a conduit protection feature integrated with the port body, wherein the conduit protection feature comprises an arcuate recess formed in an exterior surface of the sidewall of the port body into which the conduit is removably disposed and a plurality of tabs in an alternating arrangement along the top and bottom of the recess, wherein the tabs and recess are configured such that the conduit must be compressed or deformed to fit into the recess, thereby providing friction between the conduit and the tabs and the recess that substantially resists sliding of conduit in the recess, wherein the recess extends radially inwardly into the sidewall of the port body, wherein the conduit protection feature is configured to guide the conduit in a second direction transverse to the first direction, and wherein the conduit protection feature is configured to protect against one or more of the following conditions:
(i) kinking of the conduit after the conduit is coupled with the connector and after the port body is implanted in a patient,
(ii) decoupling of the conduit from the connector after the conduit is coupled with the connector and after the port body is implanted in a patient, and
(iii) penetration of the conduit adjacent to the port body by a needle after the conduit is coupled with the connector and after the port body is implanted in a patient.

2. The apparatus of claim 1, wherein the recess is defined at least in part by an upper shelf section and a lower shelf section, wherein the recess is configured to receive a conduit between the upper shelf section and the lower shelf section.

3. The apparatus of claim 1, wherein the recess is configured to be operable as a channel defined along a portion of the exterior surface of the port body.

4. The apparatus of claim 1, wherein the connector has a bent configuration.

5. The apparatus of claim 4, wherein the connector has an L-shape.

6. The apparatus of claim 1, further comprising a bell-shaped shroud associated with the port body.

7. The apparatus of claim 6, wherein the shroud at least partially surrounds the connector.

8. The apparatus of claim 6, wherein the shroud includes a generally convex outer rim and a generally convex interior surface.

9. The apparatus of claim 1, wherein the conduit protection feature comprises a sleeve and a strain relief, wherein the sleeve is configured to reinforce a coupling of the connector and a conduit, wherein the strain relief comprises a plurality of plate members configured to restrict the degree to which the strain relief may be bent transversely thereby relieving transverse stresses in a conduit coupled with the connector.

10. The apparatus of claim 1, further comprising a gastric band and a conduit, wherein the port body forms part of an injection port, wherein the gastric band, the conduit, and the injection port are coupled in a closed fluid circuit.

11. A method of implanting a gastric band system, wherein the gastric band system comprises an injection port, a gastric band, and a conduit coupling the injection port with the gastric band, wherein the injection port comprises an arcuate channel formed in an exterior surface of a sidewall of the injection port and a plurality of tabs in an alternating arrangement along the top and bottom of the channel, wherein the injection port further comprises a connector, wherein the connector and the channel are oriented along different paths, the method comprising:
(a) installing the gastric band in the patient at a first location in the patient;
(b) installing the conduit in the patient to provide a path for fluid communication between the injection port and the gastric band;
(c) installing the injection port in a patient at a second location in the patient;
(d) passing the conduit through the channel formed in the sidewall of the injection port such that the conduit is substantially disposed between the sidewall of the injection port and the plurality of tabs, wherein the act of passing the conduit through the channel comprises compressing or deforming the conduit to fit into the channel, thereby providing friction between the conduit and the tabs and the channel that substantially resists sliding of conduit in the channel;
(e) bending a portion of the conduit such that the conduit may be coupled to the connector of the injection port and pass through the channel; and
(f) connecting the conduit to the connector such that the bent portion of the conduit is located between the connector and the channel and such that the conduit extends along the different paths.

\* \* \* \* \*